(12) United States Patent
Erkens et al.

(10) Patent No.: US 11,077,034 B2
(45) Date of Patent: Aug. 3, 2021

(54) CARE CONDITIONER WITH A LOW WATER CONTENT IN A POUCH

(71) Applicant: Henkel AG & Co. KGaA, Duesseldorf (DE)

(72) Inventors: Udo Erkens, Willich (DE); Torsten Lechner, Langenfeld (DE); Thomas Schroeder, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/163,353

(22) Filed: Oct. 17, 2018

(65) Prior Publication Data
US 2019/0110966 A1    Apr. 18, 2019

(30) Foreign Application Priority Data
Oct. 18, 2017    (DE) .................... 10 2017 218 594.5

(51) Int. Cl.
| | | |
|---|---|---|
| *A61K 8/00* | (2006.01) | |
| *A61K 8/34* | (2006.01) | |
| *A61K 8/37* | (2006.01) | |
| *A61K 8/81* | (2006.01) | |
| *C11D 3/00* | (2006.01) | |
| *C08L 91/00* | (2006.01) | |
| *A61Q 5/02* | (2006.01) | |
| *A61Q 5/12* | (2006.01) | |
| *C11D 3/20* | (2006.01) | |
| *C11D 17/04* | (2006.01) | |
| *C08L 3/08* | (2006.01) | |
| *C08L 3/04* | (2006.01) | |
| *C08L 29/04* | (2006.01) | |
| *C08L 31/04* | (2006.01) | |

(52) U.S. Cl.
CPC ............... *A61K 8/342* (2013.01); *A61K 8/37* (2013.01); *A61K 8/375* (2013.01); *A61K 8/8135* (2013.01); *A61Q 5/02* (2013.01); *A61Q 5/12* (2013.01); *C08L 91/00* (2013.01); *C11D 3/0015* (2013.01); *C11D 3/2013* (2013.01); *C11D 3/2093* (2013.01); *C11D 17/043* (2013.01); *A61K 2800/596* (2013.01); *A61K 2800/87* (2013.01); *C08L 3/04* (2013.01); *C08L 3/08* (2013.01); *C08L 29/04* (2013.01); *C08L 31/04* (2013.01)

(58) Field of Classification Search
CPC .......... A61K 8/342; A61K 8/37; C11D 3/2013
See application file for complete search history.

(56) References Cited

U.S. PATENT DOCUMENTS

2013/0149271 A1* 6/2013 Van Gogh ............... A61K 8/65
                                                                424/70.9
2017/0298216 A1* 10/2017 Labeque ................ B65B 47/02

FOREIGN PATENT DOCUMENTS

| GB | 2382350 A | 5/2003 |
|---|---|---|
| WO | 2016000128 A1 | 1/2016 |
| WO | 2016061069 A2 | 4/2016 |
| WO | 2016179096 A1 | 11/2016 |
| WO | 2018081494 A2 | 5/2018 |

* cited by examiner

*Primary Examiner* — Necholus Ogden, Jr.
(74) *Attorney, Agent, or Firm* — Lorenz & Kopf, LLP

(57) ABSTRACT

The present disclosure relates to a product for care of keratinic fibers, in particular human hair, comprising a bag (pouch) comprising at least one sealed chamber, wherein the sealed chamber comprises at least one wall of one water-soluble film, and a conditioner composition which is in the sealed chamber of the bag (pouch) wherein the conditioner composition contains, based on its total weight (iia) from about 0 to about 20 wt % water and (iib) at least one fatty ingredient from the group of $C_8$-$C_{30}$ fatty alcohols and $C_8$-$C_{30}$ fatty acid triglycerides.

20 Claims, No Drawings

CARE CONDITIONER WITH A LOW WATER CONTENT IN A POUCH

CROSS-REFERENCE TO RELATED APPLICATION

This application claims priority to German Patent Application No. 10 2017 218 594.5, filed Oct. 18, 2017, which is incorporated herein by reference in its entirety.

TECHNICAL FIELD

The present disclosure relates to a cosmetic product for care and conditioning of keratinic fibers, in particular human hair, comprising a bag (pouch) having at least one chamber wherein the pouch, i.e., the chamber of the pouch is made of a water-soluble film. Packaged in this at least one chamber there is a conditioner composition, which is fabricated to have a low-water content to none at all and contains at least one fatty ingredient from the group of fatty alcohols and fatty acid triglycerides.

BACKGROUND

Water-soluble polymer films are already known from the state of the art as packaging materials. For example, portions of liquid detergents or liquid dishwashing agents may be packaged in these films and made available to the user as a single use in this form. The user can then add these bags, pouches or pods directly to the washing machine or the dishwashing machine. The film then dissolves during use, thereby releasing its contents.

For the user, this form of dosing offers various advantages. The risk of overdosing is bypassed, and the user need not dispose of the package separately thanks to the complete dissolution of the film. This form of dosing and application is therefore particularly convenient for the user.

WO 2016/061069 A2 describes pouches with liquid detergents. In principle this specification also discloses the finishing in the form of a care product. However, the application forms known so far are still associated with various disadvantages.

The single use in the form of a pouch in the area of cosmetics makes very specific requirements of the formulations contained in the pouch, in particular in the case of conditioner formulations.

A conditioner is used to condition and care for hair and therefore contains one or more care ingredients. Fatty alcohols and/or fatty acid triglycerides, for example, may be used to increase the feel and luster of hair.

The wall of the pouch is made of a water-soluble film. To prevent premature dissolution, the water content of the formulation in the pouch must therefore be as low as possible.

If the user then uses the product as contemplated herein, first the low-water or waterless conditioner composition must be released by dissolving the film. During this process, the conditioner composition comes in contact with water and is thereby diluted. The "dilute" conditioner composition, which has a much higher water content than the original compositions stored in the pouch, is applied to the hair. To ensure good usability and a high care performance, the conditioner composition must be rapidly and uniformly dilutable with water when mixed, and the viscosity of both the undiluted composition and the diluted composition should be in the optimum range for use. In addition, the conditioner should also be in a homogenous visually attractive emulsion even after being diluted.

BRIEF SUMMARY

Cosmetic products for care of keratinic fibers and methods for care and conditioning of hair are provided. In an embodiment, a cosmetic product for care of keratinic fibers includes (i) a bag that includes at least one sealed chamber, wherein the sealed chamber includes at least one wall of one water-soluble film, and (ii) a conditioner composition which is in the sealed chamber of the bag. The conditioner composition includes, based on its total weight, (iia) from about 0 to about 20 wt % water and (iib) at least one fatty ingredient from the group of $C_8$-$C_{30}$ fatty alcohols and $C_8$-$C_{30}$ fatty acid triglycerides.

In another embodiment, a cosmetic product for care of keratinic fibers includes (i) a bag that includes at least one sealed chamber, wherein the sealed chamber includes at least one wall of one water-soluble film. At least about 50 wt % of the water-soluble film includes (ia) a polymer mixture including (iaa) a first vinyl alcohol/vinyl acetate copolymer and (iab) a second vinyl alcohol/vinyl acetate copolymer which is different from the first vinyl alcohol/vinyl acetate copolymer. The water-soluble film further comprises (ib) at least one water-soluble polysaccharide chosen from the group of hydroxypropyl starches. The cosmetic product further includes (ii) a conditioner composition which is in the sealed chamber of the bag. The conditioner composition includes, based on its total weight, (iia) from about 5 to about 10 wt % water, (iib) at least one fatty ingredient from the group of $C_8$-$C_{14}$ fatty alcohols and $C_8$-$C_{14}$ fatty acid triglycerides, and (iic) one or more cationic surfactants.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was therefore to provide a cosmetic product which can be used in the form of a (bag) pouch and which has a good conditioner effect and a high care performance. The product should be aesthetically attractive during the entire period of application and should be in the form of a homogenous uniform emulsion. Furthermore, dilution with water should take place rapidly and separation of the emulsion as well as inhomogeneities should be prevented.

It has now surprisingly been found that conditioners in the form of a pouch can be made available if a water-soluble film is used to produce the pouch and if the conditioners contain a certain amount of water and at least one fatty ingredient from the group of fatty alcohols and fatty acid triglycerides.

A first subject matter of the present disclosure is a cosmetic product for care of keratinic fibers, in particular human hair, comprising
(i) a bag (pouch) comprising at least one sealed chamber, wherein the sealed chamber comprises at least one wall of one water-soluble film, and
(ii) a conditioner composition, which is provided in the sealed chamber of the bag (pouch) wherein the conditioner composition contains, based on its total weight:
   (iia) from about 0 to about 20 wt % water and (iib) at least one fatty ingredient from the group of $C_8$-$C_{30}$ fatty alcohols and $C_8$-$C_{30}$ fatty acid triglycerides.

Keratinic Fibers

The product as contemplated herein is a product for cleaning and care of keratinic fibers, in particular human hair. Keratinic fibers are understood to include wool, furs, feathers and in particular human hair.

Bag (Pouch)

The cosmetic product as contemplated herein comprises at least one bag (pouch), which in turn comprises at least one sealed chamber. The chamber(s) comprise(s) at least one wall, such as a water-soluble film comprises.

In other words, the pouch is preferably made of a water-soluble film and forms at least one chamber, wherein the chamber is sealed and/or closed. The conditioner composition as contemplated herein is packaged in the water-soluble film, so it is present in the sealed chamber of the pouch.

Therefore, in other words, the first subject matter of the present disclosure is a cosmetic product for care of keratinic fibers, in particular human hair, comprising (i) a bag (pouch) comprising at least one sealed chamber made of a water-soluble film and
(ii) a conditioner composition, which is contained in the sealed chamber of the bag (pouch), wherein the conditioner composition contains, based on its total weight
   (iia) from about 0 to about 20 wt % water and
   (iib) at least one fatty ingredient from the group of $C_8$-$C_{30}$ fatty alcohols and
   $C_8$-$C_{30}$ fatty acid triglycerides.

The first subject matter of the present disclosure is therefore in other words a cosmetic product for care of keratinic fibers, in particular human hair comprising (i) a bag (pouch) comprising at least one sealed chamber, wherein the sealed chamber is made of a water-soluble film and
(ii) a conditioner composition, which is contained in the sealed chamber of the bag (pouch), wherein the conditioner composition contains, based on its total weight
   (iia) from about 0 to about 20 wt % water
   (iib) at least one fatty ingredient from the group of $C_8$-$C_{30}$ fatty alcohols and $C_8$-$C_{30}$ fatty acid triglycerides.

The pouch here may comprise only one chamber. It is also contemplated that the pouch also comprises multiple chambers. If the pouch comprises multiple chambers, then they preferably contain formulations with different compositions.

The preparations of different compositions are then packaged separately in the water-soluble film, i.e., in a two-chamber bag (pouch) in which two preparations are packaged separately from one another but the chambers are connected to one another by film or the chambers have a film between them as a partition.

The pouch especially preferably comprises exactly one sealed chamber.

Water-Soluble Film

For production of water-soluble films, polyvinyl alcohol (PVOH) is often used. Polyvinyl alcohol is a thermoplastic material usually produced by saponification (hydrolysis) of polyvinyl acetate (PVAC). Direct synthesis (i.e., by polycondensation of vinyl alcohol) is impossible. Polyvinyl alcohol is stable in the presence of almost all anhydrous organic solvents.

In a preferred embodiment, the product as contemplated herein therefore comprises a bag (pouch), wherein the pouch (and/or the sealed chamber of the pouch) is produced from a water-soluble film, comprises a polyvinyl alcohol polymer, a polyvinyl alcohol copolymer or a mixture of several polyvinyl alcohols polymers and/or polyvinyl alcohol copolymers.

In a particularly preferred embodiment, a product as contemplated herein is exemplified in that
(ia) the soluble film comprises one or more polyvinyl alcohol polymers (PVOH polymers) and/or polyvinyl alcohol copolymers (PVOH copolymers).

In production of the polyvinyl alcohol from polyvinyl acetate, the acetyl groups can be split off either by acid or alkaline hydrolysis.

Completely hydrolyzed polyvinyl alcohol in which all the acetyl groups have been converted to hydroxyl groups is a highly crystalline polymer in which strong hydrogen bridge bonds are formed. Completely hydrolyzed polyvinyl alcohol has a high mechanical stability but will dissolve only in hot water.

If a certain amount of acetyl groups remain unchanged in the polymer of polyvinyl acetate, the result is a copolymer of polyvinyl alcohol, which is also referred to as being partially saponified or partially hydrolyzed. Since the hydrolysis is only partial, there is a decline in the number of hydrogen bridges and also in the crystallinity, and the polymer will dissolve even in cold water. Partially saponified types of polyvinyl alcohol (PVOH) with approx. 10 to about 20 wt % polyvinyl acetate (PVAC) are especially readily water-soluble.

The degree of hydrolysis of the polyvinyl alcohol may be from about 75% to about 99%, for example. The percentage amounts here mean that about 75% of the vinyl acetate units used have been hydrolyzed and converted to the corresponding hydroxyl groups. The degree of hydrolysis is preferably from about 79% to about 92%, most especially preferably the degree of hydrolysis is from about 90% to about 99%.

The degree of hydrolysis (or the degree of deacetylation) can be determined, for example, by measuring the polymer by employing quantitative $^1$H-NMR and/or $^{13}$C-NMR spectroscopy and comparison with a completely acetylated or deacetylated reference polymer or some other suitable standard.

In production of the water-soluble film, polyvinyl alcohol polymers (PVOH polymers) and/or polyvinyl alcohol copolymers (PVOH copolymers) are preferably used. If the aforementioned polymers can be processed in mixture with other polymers to form the film, then the PVOH polymer and/or the PVOH copolymer is especially preferably used as the main ingredient(s) of the film. It is thus especially preferable if the water-soluble film, based on its total weight, includes at least about 50 wt %, preferably at least about 60 wt %, more preferably at least about 70 wt % and most especially preferably at least about 85% of one or more polyvinyl alcohol polymers (PVOH polymers) and/or polyvinyl alcohol copolymers (PVOH copolymers).

In other words, the minimum amount of all PVOH polymers and PVOH copolymers used in production of the film is preferably at least about 50 wt %. The quantitative amount in wt % here is based on the total weight of the film.

In a particularly preferred embodiment, a product as contemplated herein is exemplified in that
(ia) the water-soluble film, based on its total weight, includes at least about 50%, preferably at least about 60 wt %, more preferably at least about 70 wt % and most especially preferably at least about 85 wt % of one or more polyvinyl alcohol polymers (PVOH polymers) and/or polyvinyl alcohol copolymers (PVOH copolymers).

The polyvinyl alcohol polymers (PVOH polymers) are understood as contemplated herein to be the homopolymer of polyvinyl alcohol, i.e., in formal terms the polymer is constructed exclusively of repeating units of the vinyl alcohol.

A copolymer is a polymer containing structurally different monomer units (or repeating units). A copolymer is comprises of at least two structurally different repeating units.

A polyvinyl alcohol copolymer (PVOH copolymer) as contemplated herein having two different monomer units is a polymer comprising repeating units starting from vinyl alcohol and vinyl acetate, for example. The partially hydrolyzed polyvinyl alcohol polymer described above is thus a polyvinyl alcohol copolymer (PVOH copolymer) as contemplated herein, which is referred to below as a polyvinyl alcohol/polyvinyl acetate copolymer.

A particularly preferred product is therefore exemplified in that
(ia) the water-soluble film comprises one or more polyvinyl alcohol/polyvinyl acetate copolymers.

A copolymer of polyvinyl alcohol may also comprise a third structurally different monomer unit (or repeating unit) in addition to vinyl acetate. Suitable polyvinyl alcohol copolymers of this category that can be mentioned include:
  Copolymers of vinyl alcohol, vinyl acetate and maleic acid
  Copolymers of vinyl alcohol, vinyl acetate and maleic acid esters
  Copolymers of vinyl alcohol, vinyl acetate and fumaric acid
  Copolymers of vinyl alcohol, vinyl acetate and itaconic acid
  Copolymers of vinyl alcohol, vinyl acetate and vinylsulfonic acid
  Copolymers of vinyl alcohol, vinyl acetate and 2-acrylamido-1-methylpropanesulfonic acid
  Copolymers of vinyl alcohol, vinyl acetate and 2-acrylamido-2-methylpropanesulfonic acid
  Copolymers of vinyl alcohol, vinyl acetate and acrylamide
  Copolymers of vinyl alcohol, vinyl acetate and (meth)acrylic acid
  Copolymers of vinyl alcohol, vinyl acetate and (meth)acrylic acid ester.

To produce the water-soluble film, a polyvinyl alcohol polymer or polyvinyl alcohol copolymer may be used. However, it is also possible to use different polymers in producing the film. A mixture of different polymers in this context is also referred to as a "blend."

Films of polymer blends, i.e., films comprising a plurality of different polymers may have substantial advantages with regard to water solubility and the use properties.

For example, a blend (i.e., a polymer mixture) of different polyvinyl alcohol/polyvinyl acetate copolymers with different viscosities can be used to produce the water-soluble blend. The viscosity of the polymer here is understood to be the viscosity of a standardized solution of the polymer.

To determine the viscosity, the following method is recognized internationally. The polyvinyl alcohol/polyvinyl acetate copolymer is dissolved in water at 20° C. to yield a 4% solution. All the viscosities are given in cP and are based on the viscosity of the 4% solution (amount given in wt %) in water at a temperature of 20° C. The measurement is performed in a Brookfield LV viscometer with a UL adapter. With respect to the exact procedure for measuring viscosity, reference is made to the complete contents of WO 2016/061069 A2.

The viscosity of the respective polyvinyl alcohol/polyvinyl acetate copolymer correlates with its molecular weight ("weight-average molecular weight"), so that the molecular weight of the polymer can also be estimated, based on the viscosity.

For example, a polyvinyl alcohol/polyvinyl acetate copolymer may be used to produce the water-soluble film, such that said copolymer has a viscosity of from about 3.0 to about 27.0 cP, preferably from about 4.0 to about 24.0 cP, more preferably from about 4.0 to about 23.0 cP and most especially preferably from about 4.0 to about 15.0 cP (each measured at 20° C. under the conditions described above).

If a blend of various vinyl alcohol/vinyl acetate copolymers is used, then two different vinyl alcohol/vinyl acetate copolymers may be mixed together. Then the water-soluble film is produced from this mixture.

The two polyvinyl alcohol/polyvinyl acetate copolymers may differ from one another with regard to their degree of hydrolysis or also with regard to their viscosity (and accordingly with regard to their molecular weight).

The molecular weight of a polyvinyl alcohol/polyvinyl acetate copolymer may be for example in a range from about 30,000 to about 170,000 g/mol, preferably from about 30,000 to about 120,000 g/mol and especially preferably from about 35,000 to about 100,000 g/mol (the averages and molecular weights are given). The molecular weight of the polymer can also be determined for example by gel permeation chromatography.

Therefore, a particularly preferred product is exemplified in that
(ia) the water-soluble film comprises one or more vinyl alcohol/vinyl acetate copolymers with a molecular weight of from about 30,000 to about 170,000 g/mol, preferably from about 30,000 to about 120,000 g/mol and especially preferably from about 35,000 to about 100,000 g/mol (given as the average molecular weight).

The water-soluble film is most especially preferably prepared from a polymer mixture, comprising a first vinyl alcohol/vinyl acetate copolymer and additionally comprising a second vinyl alcohol/vinyl acetate copolymer, which is different from the first polymer.

In a particularly preferred embodiment, a product as contemplated herein is exemplified in that
(ia) the water-soluble film comprises a polymer mixture of
  (iaa) a first vinyl alcohol/vinyl acetate copolymer and
  (iab) a second vinyl alcohol/vinyl acetate copolymer, which is different from the first vinyl alcohol/vinyl acetate copolymer (iaa).

The variety of polymers is understood as contemplated herein to mean that the polymers are structurally different, which may be manifested, for example, in
  a different high degree of hydrolysis and/or
  a different viscosity (measured under the specified conditions)
and/or
  a different composition of repeating units.

As described previously, water-soluble film preferably includes at least about 80 wt % PVOH polymer and/or PVOH copolymers. In addition to the PVOH (co)polymers, the film may also comprise other ingredients. Thus the film may also contain plasticizers, fillers, crosslinking agents, pigments and/or bitter substances.

Adding plasticizers can increase the flexibility of the film. The usual plasticizers include for example glycerol, diglycerol, sorbitol, ethylene glycol, diethylene glycol, propylene glycol, dipropylene glycol, polyethylene glycols (with a molecular weight of up to about 400 g/mol).

The film may also contain additional polymers which may be used for example as fillers. The use of additional polymers may also result in the film having a higher resistance to chemicals and/or the ingredients that should be packaged in the chamber of the pouch.

Polymers that can additionally be used including, for example, polysaccharides such as methyl cellulose, carboxymethyl cellulose, ethyl cellulose, hydroxyethyl cellulose, hydroxypropyl cellulose, hydroxypropylmethyl cellulose, dextrin and hydroxypropyl starch, especially preferably at least one water-soluble polysaccharide from the group of hydroxypropyl starches. Polyvinylpyrrolidones (which may be crosslinked or uncrosslinked) may be used as additional polymers.

It is most especially preferable if the films additionally contain at least one polysaccharide.

In a most especially preferred embodiment, a product as contemplated herein is exemplified in that the water-soluble film comprises:
(ia) one or more vinyl alcohol/vinyl acetate copolymers and
(ib) at least one optionally modified polysaccharide, preferably at least one polysaccharide from the group of methyl cellulose, carboxymethyl cellulose, ethyl cellulose, hydroxyethyl cellulose, hydroxypropyl cellulose, hydroxypropylmethyl cellulose, dextrin and hydroxypropyl starch, especially preferably at least one water-soluble polysaccharide from the group of hydroxypropyl starches.

Additional suitable fillers which may be present in the water-soluble film include silica, metal oxides, calcium carbonate, talc and mica.

The thickness of the water-soluble film(s) used to produce the pouches and/or for packaging the shampoo preparation preferably amounts to from about 0.01 to about 0.1 mm, preferably from about 0.01 to about 0.08 mm and in particular from about 0.02 to about 0.06 mm.

Determining the Water Solubility of the Film

The product as contemplated herein comprises a bag (pouch), which forms at least one sealed chamber. The wall of the pouch (and thus of the chamber) is produced from a water-soluble film.

It is essential here for the film to be water-soluble so that the pouch will dissolve during use of the product (for example, for shampooing hair or in the shower).

The water solubility is determined here by the following method:
Material
Glass beaker (600 mL)
Magnetic stirrer (for example Labline model no. 1250 or equivalent) and stirrer 5 cm
Thermometer (0-100° C.)
Stopwatch (0-300 s)
Polaroid 35 mm transparency holder
Clamps and stand
Distilled water (20° C.)
Method Pieces of the size 3.8×3.2 cm are cut from the film whose water solubility is to be determined. These pieces are inserted into the transparency holder. The glass beaker is filled with 500 mL distilled water. The filling level of the glass is marked on the glass beaker. Then the glass beaker is placed on the magnetic stirrer, the stirring mechanism is added and the magnetic stirrer is placed on a stage which creates a water eddy in the glass beaker so that the water eddy constitutes one fifth of the original filling level. The transparency holder, which is assembled with the film, is inserted into the glass beaker using clamps, so that the long end of the transparency holder is lines up in parallel with the surface of the water. The transparency holder here should be immersed so far into the water that the top edge of the transparency holder is 0.6 cm below the surface of the moving water. The short side of the transparency holder should be next to the wall of the glass beaker and the other side should be lined up directly above the stirring mechanism.

The stopwatch is started when the transparency holder is immersed in water. The film disintegrates when a tear appears. As soon as all the visible parts have been removed from the transparency holder, the transparency holder is removed from the glass beaker. Dissolution has taken place as soon as no more film fragments are visible and as soon as the solution has become clear.

A film as contemplated herein is water-soluble if dissolution according to the aforementioned method takes place within about 300 seconds (measurement carried out at 20° C.).

The dissolution of the film when the measurement is carried out according to the method described above takes place within about 250 seconds, more preferably within about 200 seconds and especially preferably within about 150 seconds.

Production of the Film and the Pouch

To produce at least one sealed chamber of the pouch, the water-soluble film described previously is used, wherein the film comprises the polymers described above.

For example, the polymers can be blended together first—optionally with a thermal treatment. This is how the polymer blend is prepared. Then the film can be shaped from the polymers and/or the polymer blend, wherein the shaping can take place for example by casting, extrusion, rolling and the like.

A pouch is now shaped from this film by forming at least one sealed chamber from the film. The chamber can be formed by the methods familiar to those skilled in the art. For example, parisons or preforms can be formed from the water-soluble film first. These are then subjected to a blow-molding pressure, wherein the parison is sent to the different processing stations of a blow-molding machine. Typically such a blow-molding machine has a heat treatment as well as a blow-molding device in the area in which the parison, previously regulated at a temperature, is expanded by biaxial orientation to form a container. This expansion takes place with the help of compressed air which is introduced into the expanding parison. During the development of the chamber, it is filled with shampoo and sealed in one embodiment.

The sealing can take place for example by melting and pressing at the seams of the pouch.

Conditioner Composition

A care and conditioning conditioner composition is provided in at least one sealed chamber of the pouch (bag). The exemplifying feature of the conditioner composition is its low water content and its content of at least one fatty ingredient from the group of $C_8$-$C_{30}$ fatty alcohols and $C_8$-$C_{30}$ fatty acid triglycerides.

Water Content

To prevent premature dissolution of the water-soluble film, the conditioner formulation as contemplated herein is formulated to be anhydrous or with a low water content. This means that the water content (iia) of the conditioner is max. about 20 wt %. The water content which is given here in wt % is based on the total amount of conditioner.

The lower the water content of the conditioner composition, the better the unwanted premature dissolution of the water-soluble film can be prevented. On the other hand, however, a certain low-dose water content can also simplify the dilution process taking place in the application. For this reason, it is most especially preferred for the water content to be adjusted to a very specific low range.

The conditioner preferably contains—based on its total weight—from about 0 to about 19 wt %, preferably from about 3 to about 19 wt %, more preferably from about 4 to about 19 wt %, even more preferably from about 4 to about 12 wt % and most especially preferably from about 5 to about 10 wt % water.

In another most especially preferred embodiment, a product as contemplated herein is exemplified in that the (ii) Conditioner composition, which is provided in the sealed chamber of the bag (pouch) contains—based on its weight—

(iia) from about 0 to about 19 wt %, preferably from about 3 to about 19 wt %, more preferably from about 4 to about 19 wt %, even more preferably from about 4 to about 12 wt % and most especially preferably from about 5 to about 10 wt % water.

Fatty Ingredient

To achieve the conditioning effect, high luster and a pleasant feel, the conditioner composition as contemplated herein contains (ii) at least one fatty ingredient from the group of $C_8$-$C_{30}$ fatty alcohols and $C_8$-$C_{30}$ fatty acid triglycerides (iib).

"Fatty ingredients" are understood as contemplated herein to be organic compounds with a solubility in water at room temperature (22° C.) and atmospheric pressure (760 mmHg) of less than about 1 wt %, preferably less than about 0.1 wt %. Explicitly only uncharged (i.e., nonionic) compounds fall under the definition of fatty ingredients. Fatty ingredients have at least one saturated or unsaturated alkyl group with at least eight carbon atoms. The molecular weight of the fatty ingredients is max. about 5000 g/mol, preferably max. about 2500 g/mol and especially preferably max. about 1000 g/mol. The fatty ingredients are neither polyalkoxylated nor polyglycerylated compounds.

In this context, the fatty ingredients as contemplated herein are understood to be from the group OF $C_8$-$C_{30}$ fatty alcohols and $C_8$-$C_{30}$ fatty acid triglycerides. In the sense of the present disclosure, explicitly only nonionic substances are considered to be fatty ingredients. Charged compounds such as fatty acids and their salts are not understood to be fatty ingredients.

The $C_8$-$C_{30}$ fatty alcohols may be saturated, monounsaturated or polyunsaturated, linear or branched fatty alcohols with from about 8 to about 30 carbon atoms.

Examples of suitable linear, saturated $C_8$-$C_{30}$ fatty alcohols include octan-1-ol, decan-1-ol, dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Suitable linear unsaturated fatty alcohols include (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linoleyl alcohol), gadoleyl alcohol ((9Z)-eicos-9-en-1-ol), arachidonic alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

A $C_8$-$C_{30}$ fatty acid triglyceride is understood in the sense of the present disclosure to be the triester of the trivalent alcohol glycerol with three equivalents of fatty acid. Then both different and structurally identical fatty acids as well as different fatty acids within a triglyceride molecule may be involved in the formation of esters.

Fatty acids as contemplated herein are understood to refer to saturated or unsaturated, branched or unbranched $C_8$-$C_{30}$ carboxylic acids. Unsaturated fatty acids may be mono- or polyunsaturated. In the case of an unsaturated fatty acid, its C—C double bond(s) may have the cis- or trans-configuration.

The fatty acid triglycerides are exemplified by good suitability in which the three ester groups are formed by starting with glycerol with fatty acids selected from octanoic acid (caprylic acid), decanoic acid (capric acid), dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidonic acid), docosanoic acid (behenic acid), petroselinic acid [(Z)-6-octadecenic acid], palmitoleic acid [(9Z)-hexadec-9-ene acid], oleic acid [(9Z)-octadec-9-enoic acid], elaidic acid [(9e)-octadec-9-ene acid], erucaic acid [(13Z)-docos-13-ene acid], linoleic acid [(9Z,12Z)-octadeca-9,12-dienoic acid, linolenic acid [(9Z,12Z,15Z)-octadeca-9,12,15-trienic acid, eleostearic acid [(9Z,11E,13E)-octadeca-9,11,3-trienic acid], arachidonic acid [(5Z,8Z,11Z,14Z)-eicosa-5,8,11,14-tetraenoic acid] and/or nervonic acid [(15Z)-tetracos-15-enoic acid].

The fatty acid triglycerides may also be of natural origin. The fatty acid triglycerides and/or mixtures thereof that may occur in hardened castor oil in soy oil, peanut oil, olive oil, sunflower oil, macadamia oil, moringa oil, apricot kernel oil, marula oil and/or optionally hardened castor oil and/or mixtures thereof are especially suitable for use in the product as contemplated herein.

Within the scope of the work leading to this present disclosure, it has been found that the short-chain fatty alcohols in particular, i.e., the $C_8$-$C_{14}$ fatty alcohols, can be incorporated very well into anhydrous or low-water emulsions, which can be diluted well, quickly and homogeneously with water in the subsequent application.

Short-chain fatty acid triglycerides, i.e., the triesters of glycerol with three equivalents of a $C_8$-$C_{14}$ fatty acid have led to a stable and easily dilutable formulation when incorporated into the low water and/or anhydrous conditioner.

In another most especially preferred embodiment, a product as contemplated herein is exemplified in that the conditioner composition, which is provided in the sealed chamber of the bag (pouch) contains:

(iib) at least one fatty ingredient from the group of $C_8$-$C_{14}$ fatty alcohols and $C_8$-$C_{14}$ fatty acid triglycerides.

Short-chain fatty alcohols, which are most particularly suitable for solving the problem as contemplated herein, may be selected from the group of octan-1-ol, decan-1-ol, dodecan-1-ol (dodecyl alcohol, lauryl alcohol) and tetradecan-1-ol (tetradecyl alcohol, myristyl alcohol).

In another most especially preferred embodiment, a product as contemplated herein is exemplified in that the conditioner composition, which is provided in the sealed chamber of the bag (pouch) contains:

(iib) at least one fatty ingredient from the group of octan-1-ol, decan-1-ol, dodecan-1-ol (dodecyl alcohol, lauryl alcohol) and tetradecan-1-ol (tetradecyl alcohol, myristyl alcohol).

Suitable representatives of $C_8$-$C_{30}$ fatty acid triglycerides fall under the general formula (F1)

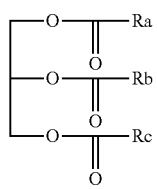

(F1)

wherein

Ra, Rb, Rc independently of one another stand for a saturated or unsaturated, branched or unbranched $C_7$-$C_{29}$ alkyl group.

Suitable saturated fatty acids in this composition may be selected from

| Fatty acid | Ra, Rb and/or Rc= |
| --- | --- |
| Octanoic acid (caprylic acid) | —$C_7H_{15}$ |
| Decanoic acid (capric acid) | —$C_9H_{19}$ |
| Dodecanoic acid (lauric acid) | —$C_{11}H_{23}$ |
| Tetradecanoic acid (myristic acid) | —$C_{13}H_{27}$ |
| Hexadecanoic acid (palmitic acid) | —$C_{15}H_{31}$ |
| Octadecanoic acid (stearic acid) | —$C_{17}H_{35}$ |
| Eicosanoic acid (arachidonic acid) | —$C_{19}H_{39}$ |
| Docosanoic acid (behenic acid) | —$C_{21}H_{43}$ |
| Tetracosanoic acid (lignoceric acid) | —$C_{23}H_{47}$ |

Suitable unsaturated fatty acids in this composition may be selected from

In another most especially preferred embodiment, a product as contemplated herein is exemplified in that the conditioner composition, which is provided in the sealed chamber of the bag (pouch) contains (iib) at least one fatty ingredient from the group of $C_8$-$C_{30}$ fatty acid triglycerides of general formula (F1)

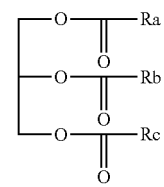

(F1)

wherein

Ra, Rb, Rc independently of one another stand for a saturated or unsaturated, branched or unbranched $C_7$-$C_{29}$ alkyl group.

Short-chain fatty acid triglycerides that are most especially suitable to solve the problems as contemplated herein can be selected from the group of triesters of glycerol or saturated unbranched $C_8$-$C_{14}$ fatty acids.

In another most especially preferred embodiment, a product as contemplated herein is exemplified in that the conditioner composition, which is provided in the sealed chamber of the bag (pouch) contains (iib) at least one fatty ingredient from the group of $C_8$-$C_{14}$ fatty acid triglycerides of general formula (F1)

| Fatty acid | Ra, Rb and/or Rc = |
| --- | --- |
| Petroselinic acid [(Z)-6-octadecenoic acid] | |
| Palmitoleic acid [(9Z)-hexadec-9-enoic acid] | |
| Oleic acid [(9Z)-octadec-9-enoic acid] | |
| Elaidic acid [(9E)-octadec-9-enoic acid] | |
| Erucaic acid [(13Z)-docos-13-enoic acid] | |
| Linoleic acid [(9Z,12Z)-octadeca-9,12-dienoic acid] | |
| Linolenic acid [(9Z,12Z,15Z)-octadeca-9,12,15-trienoic acid] | |
| Eleostearic acid [(9Z,11E,13E)-octadeca-9,11,3-trienoic acid] | |
| Arachidonic acid [(5Z,8Z,11Z,14Z)-eicosa-5,8,11,14-tetraenoic acid] | |
| Nervonic acid [(15Z)-tetracos-15-enoic acid] | |

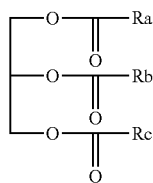

(F1)

wherein
Ra, Rb, Rc independently of one another stand for a saturated unbranched $C_7$-$C_{13}$ alkyl group.

Most especially preferably, caprylic acid triglycerides, capric acid triglycerides and caprylic acid capric acid triglycerides are used as fatty ingredients as contemplated herein.

The fatty ingredient(s) as contemplated herein is (are) preferably present in certain quantity ranges in the conditioner composition as contemplated herein.

The conditioner composition may contain the fatty ingredient(s) as contemplated herein in a total amount of from about 1.0 to about 80 wt %.

However, it is preferable if the conditioner composition contains, based on its total weight, one or more of the fatty ingredients as contemplated herein in a total amount of from about 10 to about 80 wt %, preferably from about 15 to about 70 wt %, more preferably from about 20 to about 70 wt % and most especially preferably from about 25 to about 70 wt %.

In a particularly preferred embodiment, a product as contemplated herein is exemplified in that the conditioner composition, which is provided in the sealed chamber of the bag (pouch) contains—based on the total weight of the conditioner composition—one or more fatty ingredients from the group of $C_8$-$C_{30}$ fatty alcohols and $C_8$-$C_{30}$ fatty acid triglycerides (iib) in a total amount of from about 10 to about 80 wt %, preferably from about 15 to about 70 wt %, more preferably from about 20 to about 70 wt % and most especially preferably from about 25 to about 70 wt %.

In an explicitly most especially preferred embodiment, a product as contemplated herein is exemplified in that the conditioner composition, which is provided in the sealed chamber of the bag (pouch) contains—based on the total weight of the conditioner composition—one or more fatty ingredients from the group of $C_8$-$C_{14}$ fatty alcohols and $C_8$-$C_{14}$ fatty acid triglycerides (iib) in a total amount of from about 10 to about 80 wt % preferably from about 15 to about 70 wt % more preferably from about 20 to about 70 wt % and most especially preferably from about 25 to about 70 wt %.

In another most especially preferred embodiment, a product as contemplated herein is exemplified in that the condition composition, which is provided in the sealed chamber of the bag (pouch) contains—based on the total weight of the conditioner composition—one or more fatty ingredients from the group of $C_8$-$C_{14}$ fatty acid triglycerides (iib) in a total amount of from about 10 to about 80 wt %, preferably from about 15 to about 70 wt %, more preferably from about 20 to about 70 wt % and most especially preferably from about 25 to about 70 wt %.

Cationic Surfactants

Conditioner formulations as contemplated herein may additionally contain one or more cationic surfactants to reinforce the care effect and to further stabilize the emulsion.

Cationic surfactants are understood to be surfactants, i.e., surface-active components, each of which has one or more positive charges. Cationic surfactants contain only positive charges (which are naturally neutralized by an anionic counterion to ensure electroneutrality). These surfactants are usually constructed from a hydrophobic part and a hydrophilic head group, wherein the hydrophobic part usually includes a hydrocarbon structure (e.g., including one or two linear or branched alkyl chains), and the positive charge(s) is (are) localized in the hydrophilic head group.

Examples of Cationic Surfactants Include
quaternary ammonium compound, which may carry one or two alkyl chains with a chain length of from about 8 to about 28 carbon atoms as the hydrophobic radicals
quaternary phosphonium salts, substituted with one or more alkyl chains with a chain length of from about 8 to about 24 carbon atoms or
tertiary sulfonium salts.

In addition, the cationic charge may also be in the form of an onium structural ingredient part of a heterocyclic ring (e.g., an imidazolium ring or a pyridinium ring).

In addition to the functional unit, which the cationic charge carries, the cationic surfactant may also contain additional uncharged functional groups, which is the case with ester quats, for example.

Preferred cationic surfactants of formula (I) include for example physiologically tolerable salts of N,N,N-trimethyl-1-hexadecaneaminium, in particular N,N,N-trimethyl-1-hexadecaneaminium chloride, which is also distributed under the brand name Dehyquart A-CA. Also preferred are salts of trimethylstearyl ammonium, in particular trimethylstearyl ammonium chloride, which is also available commercially under the brand name GenaminSTAC. Additional especially preferred cationic surfactants of formula (I) include the salts of trimethyl-1-eicosaneaminium, in particular trimethyl-1-eicosaneaminium chloride and salts of trimethyl-1-docosaneaminium, in particular trimethyl-1-docosanaminium chloride. A mixture of the two compounds is available from the Clariant Company under the brand name GenaminKDMP.

The cationic surfactant(s) is (are) most especially preferably used in certain quantity ranges in the conditioner composition as contemplated herein.

The shampoo may contain one or more cationic surfactants—in particular the aforementioned preferred and especially preferred representatives—in a total amount of from about 0.1 to about 10 wt %. All the quantity amounts given in wt % here are based on the total amount of the shampoo formulation.

However, it is preferable for the cationic surfactants are to be used in total amounts of from about 1.0 to about 14.0 wt %, more preferably from about 3.0 to about 12.0 wt %, and most especially preferably from about 5.0 to about 10.0 wt %.

In another preferred embodiment, a product as contemplated herein is exemplified in that the conditioner composition, which is provided in the sealed chamber of the bag (pouch) contains—based on the total weight of the conditioner composition
(iic) one or more cationic surfactants in a total amount of from about 0.5 to about 15.0 wt %, preferably from about 1.0 to about 14.0 wt %, more preferably from about 3.0 to about 12.0 wt % and most especially preferably from about 5.0 to about 10.0 wt %.

Solvents

The conditioner composition as contemplated herein is prepared to be anhydrous or have a low water content. Therefore, solvents and/or short-chain alcohols are preferably used as the solvent.

Examples of short-chain alcohols that may be used include alcohols with from about 2 to about 9 carbon atoms and from about 1 to about 6 hydroxyl groups The alcohol with from about 2 to about 9 carbon atoms and from about 1 to about 6 hydroxyl groups is preferably selected from at least one compound from the group of glycerol, 1,2-propanediol, 1,3-propanediol, ethanol, ethylene glycol, isopropanol, n-butanol, 1,3-butylene glycol. Especially preferred alcohols are 1,2-propanediol, 1,3-propanediol and glycerol.

The esters, starting from the aforementioned alcohols, may be used as solvents. Dipropylene glycol is especially preferred in this context.

In a most especially preferred embodiment, a product as contemplated herein is exemplified in that the conditioner composition, which is provided in the sealed chamber of the bag (pouch) contains one or more solvents from the group of dipropylene glycol, glycerol, 1,2-propanediol, 1,3-propanediol, ethanol, ethylene glycol, isopropanol n-butanol and/or 1,3-butylene glycol.

The alcohol(s) may contain—in addition to the aforementioned fatty ingredients—the carrier base or conditioner formulation and are therefore preferably present in larger quantity ranges in the conditioner formulation.

The conditioner formulation preferably contains—based on its total weight—one or more solvents in a total amount of from about 10 to about 80%, preferably from about 15 to about 70 wt %, more preferably from about 20 to about 60 wt %, and most especially preferably from about 25 to about 50 wt %.

In a most especially preferred embodiment, a product as contemplated herein is exemplified in that the conditioner composition, which is provided in the sealed chamber of the bag (pouch) contains—based on the total weight of the conditioner composition—one or more solvents in a total amount of from about 10 to about 80 wt %, preferably from about 15 to about 70 wt %, more preferably from about 20 to about 60 wt %, and most especially preferably from about 25 to about 50 wt %.

In a most especially preferred embodiment, the product as contemplated herein is exemplified in that the conditioner composition, which is provided in the sealed chamber of the bag (pouch) contains—based on the total weight of the conditioner composition—one or more solvents from the group of dipropylene glycol, glycerol, 1,2-propanediol, 1,3-propanediol, ethanol, ethylene glycol, isopropanol n-butanol and 1,3-butylene glycol in a total amount of from about 10 to about 80 wt %, preferably from about 15 to about 70 wt %, more preferably of from about 20 to about 60 wt % and most especially preferably from about 25 to about 50 wt %.

Additional Formulation Ingredients

In addition, it has proven advantageous if the conditioner contains nonionic interfacial substances. Preferred nonionic surfactants include alkyl polyglycosides as well as alkylene oxide addition products on two fatty alcohols and fatty acids each with from about 2 to about 30 mol ethylene oxide per mol fatty alcohol and/or fatty acid. Preparations with excellent properties are also obtained if they contain fatty acid esters of ethoxylated glycerol as the nonionic surfactants.

The nonionic, zwitterionic or amphoteric surfactants are used in amounts of from about 0.1 to about 45 wt %, preferably from about 1 to about 30 wt %, and most especially preferably from about 1 to about 15 wt %, based on the total amount of the ready-to-use agents.

Furthermore, the conditioners as contemplated herein may contain additional active ingredients, auxiliaries and additives, such as anionic surfactants, amphoteric and/or zwitterionic surfactants, nonionic polymers such as vinylpyrrolidinone/vinyl acrylate copolymers, polyvinylpyrrolidinone, vinylpyrrolidone/vinyl acetate copolymers, polyethylene glycols and polysiloxanes, additional silicones such as volatile or nonvolatile, linear, branched or cyclic, crosslinked or noncrosslinked polyalkylsiloxanes (such as dimethicones or cyclomethicones), polyarylsiloxanes and/or polyalkylarylsiloxanes, in particular polysiloxanes with organofunctional groups such as substituted or unsubstituted amines (amodimethicones), carboxyl, alkoxy and/or hydroxyl groups (dimethicone copolyols), linear polysiloxane (A) polyoxyalkylene (B) block copolymers, grafted silicone polymers, cationic polymers, such as quaternized cellulose ethers, polysiloxanes with quaternary groups, dimethyldiallylammonium chloride polymers, acrylamide dimethyldiallylammonium chloride copolymers, dimethylaminoethyl methacrylate-vinylpyrrolidinone copolymers quaternized with diethyl sulfate, vinylpyrrolidinone-imidazolinium-methochloride copolymers and quaternized polyvinyl alcohol, zwitterionic and amphoteric polymers, anionic polymers such as polyacrylic acids or crosslinked polyacrylic acids, structurants such as glucose, maleic acid and lactic acid, hair conditioning compounds such as phospholipids, for example, lecithin and cephalins; perfume oils, dimethyl isosorbide and cyclodextrins; fiber structure-improving active ingredients, in particular monosaccharides, disaccharides and oligosaccharides such as, for example, glucose, galactose, fructose, sucrose and lactose; dyes for coloring the agent, antidandruff active ingredients such as piroctoneolamine, zinc omadine and climbazole; amino acids and oligopeptides; animal- and/or plant-based protein hydrolyzates as well as those in the form of their fatty acid condensation products or optionally anionically or cationically modified derivatives; vegetable oils; light protectants and UV blockers; active ingredients such as panthenol, pantothenic acid, pantolactone, allantoin, pyrrolidonecarboxylic acids and the salts thereof as well as bisabolol, polyphenols, in particular hydroxycinnamic acids, 6,7-dihydroxycoumarins, hydroxybenzoic acids, catechols, tannins, leukoanthocyanidines, anthocyanidines, flavanones, flavones and flavonols; ceramides or pseudoceramides; vitamins, provitamins and vitamin precursors; plant extracts; fats and waxes such as fatty alcohols, beeswax, montane wax and paraffins; swelling and penetration substances such as glycerol, propylene glycol monoethyl ethers, carbonates, bicarbonates, guanidines, ureas and primary, secondary and tertiary phosphates, turbidity agents such as latex, styrene PVP and styrene acrylamide copolymers; pearlescent agents, such as ethylene glycol monostearate and ethylene glycol distearate as well as PEG-3 distearate; pigments as well as propellants, such as propane-butane mixtures, $N_2O$, dimethyl ether, $CO_2$ and air.

Those skilled in the art will make the choice of these additional substances according to the desired properties of the agents. With respect to additional optional components as well as the quantities of these components used, reference is made explicitly to the relevant textbooks, with which those skilled in the art are familiar. The additional active ingredients and additives are preferably used in the agents as contemplated herein in amounts of from about 0.0001 to about 25 wt % each, in particular from about 0.0005 to about 15 wt %, each based on the total weight of the dye preparation (K1) and/or the oxidizing agent preparation (K2).

Application

The product as contemplated herein is preferably applied by the user for conditioning and care of his hair. To do so, the product is wetted with water, whereupon the water-soluble film dissolves and releases the conditioner composition. Dissolution of the film usually takes place within from about 15 seconds to a few minutes. The user can support the dissolution mechanically by rubbing it between one's hands, for example. Next, the conditioner is applied to the hair, allowed to act briefly or briefly massaged into the hair and then rinsed off with water.

A second subject matter is a method for cleaning and conditioning hair, where a cosmetic product such as that disclosed in detail in the description of the first subject matter of the present disclosure is mixed with water, applied to the hair and rinsed out again after about 10 seconds to about 10 minutes.

With respect to the preferred embodiments of the method as contemplated herein, it is true mutatis mutandis what was said about the product as contemplated herein.

EXAMPLES

The conditioner preparations in the following tables were prepared (all amounts given in wt %):

|  | Ex. 1 | Ex. 2 | Ex. 3 | Ex. 4 |
|---|---|---|---|---|
| Caprylic acid/capric acid triglyceride (Neobee M-5) (CAS No. 73398-61-5) | 68.0 | — | 70.0 | 30.0 |
| Cetyl PEG/PPG-10/1 dimethicone (Abil EM 90, Evonik) | 4.0 | 4.0 | 4.0 | 4.0 |
| PEG-10 olive glyceride | 4.0 | 4.0 | 2.0 | 4.0 |
| Lauryl alcohol ($C_{12}$ fatty alcohol, 1-dodecanol) | 2.5 | 1.5 | — | 2.5 |
| Myristyl alcohol ($C_{14}$ fatty alcohol, tetradecan-1-ol) | — | — | 3.0 | 1.5 |
| Quaternum-87, propylene glycol (Varisoft W 575, Evonik) | 11.0 | 11.0 | — | 11.0 |
| Quaternium-26, propylene glycol (Ceraphyl 65, Ashland) | — | — | 4.0 | — |
| Bis-Ethyl(isostearylimidazoline) isostearamide (Keradyn HH-LQ, Croda) | — | — | 4.0 | — |
| Water | 10.0 | 10.0 | 10.0 | 10.0 |
| Citric acid | 0.05 | 0.05 | 0.05 | 0.05 |
| Trideceth-12 | 0.5 | 0.5 | 0.5 | 0.5 |
| Dipropylene glycol | to 100 | to 100 | to 100 | to 100 |

The preparations in Examples 1 through 4 were packaged in a single-chamber container (pouch) made of a water-soluble film from the company Monosol model LX 9643 (Monosol model LX 9643; water-soluble film comprising polyvinyl alcohol/polyvinyl acetate copolymer, degree of hydrolysis approx. 84%, average molecular weight 39,000 g/mol).

|  | Ex. 5 | Ex. 6 | Ex. 7 | Ex. 8 |
|---|---|---|---|---|
| Caprylic acid/capric acid triglyceride (Neobee M-5) (CAS No. 73398-61-5) | 60.0 | — | 55.0 | 46.0 |
| Cetyl PEG/PPG-10/1 dimethicone (Abil EM 90, Evonik) | 4.0 | 4.0 | 4.0 | 4.0 |
| PEG-10 olive glyceride | 4.0 | 4.0 | 2.0 | 4.0 |
| Lauryl alcohol ($C_{12}$ fatty alcohol, 1-dodecanol) | 5.5 | 10.5 | — | 2.5 |
| Myristyl alcohol ($C_{14}$ fatty alcohol, tetradecan-1-ol) | — | — | 3.0 | 8.5 |
| Quaternium-87, propylene glycol (Varisoft W 575, Evonik) | 11.0 | 11.0 | — | 11.0 |
| Quaternium-26, propylene glycol (Ceraphyl 65, Ashland) | — | — | 4.0 | — |
| Bis-Ethyl(isostearylimidazoline) isostearamide (Keradyn HH-LQ, Croda) | — | — | 4.0 | — |
| Water | 10.0 | 10.0 | 10.0 | 10.0 |
| Citric acid | 0.05 | 0.05 | 0.05 | 0.05 |
| Trideceth-12 | 0.5 | 0.5 | 0.5 | 0.5 |
| Dipropylene glycol | to 100 | to 100 | to 100 | to 100 |

The preparations in Examples 5 through 8 were packaged in a single chamber container (pouch) made of a water-soluble film from the company Monosol model SCP20633 (Monosol model SCP 20633: water-soluble film comprising polyvinyl alcohol/polyvinyl acetate copolymer, degree of hydrolysis approx. 89%, average molecular weight=95,000 g/mol).

The single chamber bag (pouch) was combined with water that was warm to the touch and kneaded using one's hands. In doing so, the film also dissolved and the conditioner formulation was released. A homogenous and uniform emulsion was obtained after mixing after with water. This conditioner formulation was applied to wet strands of hair, allowed to act for 1 minute and then rinsed off with tap water. Next the hair was dried. The hair could be combed well and had a soft feel.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A cosmetic product for care of keratin fibers comprising
   (i) a bag comprising at least one sealed chamber, wherein the sealed chamber comprises at least one wall of one water-soluble film comprising a polyvinyl alcohol/polyvinyl acetate copolymer, and
   (ii) a conditioner composition which is in the sealed chamber of the bag, wherein the conditioner composition comprises
   0 to 70 weight percent of caprylic acid/capric acid triglyceride;
   4 weight percent of cetyl PEG/PPG-10/1 dimethicone;
   2 to 4 weight percent of PEG-10 olive glyceride;
   0 to 10.5 weight percent of lauryl alcohol;
   0 to 8.5 weight percent of myristyl alcohol;
   0 to 11 weight percent of quaternium-87, propylene glycol;
   0 to 4 weight percent of quaternium-26, propylene glycol;
   0 to 4 weight percent of bis-ethyl(isostearylimidazoline) isostearamide; and
   5 to 10 weight percent of water;

wherein each weight percent is based on a total weight of the conditioner composition and the total weight equals 100 weight percent.

2. The product according to claim 1, wherein
(ia) the water-soluble film, based on the total weight, includes at least about 50% of the polyvinyl alcohol/polyvinyl acetate copolymer.

3. The product according to claim 1, wherein
the water-soluble film is a polymer mixture of
(iaa) a first polyvinyl alcohol/polyvinyl acetate copolymer and
(iab) a second polyvinyl alcohol/polyvinyl acetate copolymer, which is different from the first vinyl alcohol/vinyl acetate copolymer (iaa).

4. The product according to claim 1, wherein the water-soluble film further comprises
at least one optionally modified polysaccharide optionally chosen from the group of hydroxypropyl starches.

5. The product according to claim 1, wherein the conditioner composition, which is provided in the sealed chamber of the bag further comprises
(iib) at least one fatty ingredient from the group of octan-1-ol, decan-1-ol, dodecan-1-ol and tetradecan-1-ol.

6. The product according to claim 1, wherein the conditioner composition, which is provided in the sealed chamber of the bag further comprises an additional
(iib) $C_8$-$C_{30}$ fatty acid triglyceride of the general formula (F1)

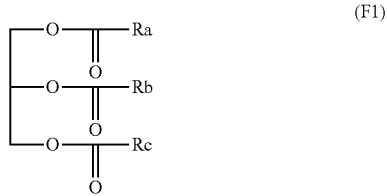

where
Ra, Rb, Rc independently of one another stand for a saturated or unsaturated, branched or unbranched $C_7$-$C_{29}$ alkyl group.

7. The product according to claim 1, wherein the conditioner composition, which is provided in the sealed chamber of the bag further comprises
(iib) at least one fatty ingredient from the group of $C_8$-$C_{14}$ fatty acid triglycerides of general formula (F1)

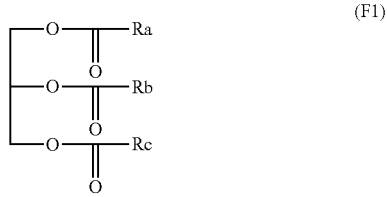

where
Ra, Rb, Rc independently of one another stand for a saturated unbranched $C_7$-$C_{13}$ alkyl group.

8. A method for care and conditioning of hair, wherein a cosmetic product according to claim 1 is mixed with water, applied to the hair and rinsed out after a treatment time of from about 10 seconds to about 10 minutes.

9. The product according to claim 1, wherein
(ia) the water-soluble film, based on the total weight, includes at least about 85 wt % of the polyvinyl alcohol/polyvinyl acetate copolymer.

10. A cosmetic product for care of keratinic fibers comprising
(i) a bag comprising at least one sealed chamber, wherein the sealed chamber comprises at least one wall of one water-soluble film comprising a polyvinyl alcohol/polyvinyl acetate copolymer, and
(ii) a conditioner composition which is in the sealed chamber of the bag, wherein the conditioner composition consists of:
0 to 70 weight percent of caprylic acid/capric acid triglyceride;
4 weight percent of cetyl PEG/PPG-10/1 dimethicone;
2 to 4 weight percent of PEG-10 olive glyceride;
0 to 10.5 weight percent of lauryl alcohol;
0 to 8.5 weight percent of myristyl alcohol;
0 to 11 weight percent of quaternium-87, propylene glycol;
0 to 4 weight percent of quaternium-26, propylene glycol;
0 to 4 weight percent of bis-ethyl(isostearylimidazoline) isostearamide;
10 weight percent of water;
0.05 weight percent of citric acid;
0.5 weight percent of trideceth-12; and
a balance of dipropylene glycol,
wherein each weight percent is based on a total weight of the conditioner composition and the total weight equals 100 weight percent.

11. The product according to claim 1 comprising 30 to 68 weight percent of the caprylic acid/capric acid triglyceride; 1.5 to 2.5 weight percent of lauryl alcohol and 1.5 to 3 weight percent of myristyl alcohol.

12. The product according to claim 1 comprising 46 to 60 weight percent of the caprylic acid/capric acid triglyceride; 2.5 to 10.5 weight percent of lauryl alcohol and 3 to 8.5 weight percent of myristyl alcohol.

13. The product according to claim 10 wherein
the caprylic acid/capric acid triglyceride is present in an amount of 68 weight percent;
the PEG-10 olive glyceride is present in an amount of 4 weight percent;
the lauryl alcohol is present in an amount of 2.5 weight percent; and
the quaternium-87, propylene glycol is present in an amount of 11 weight percent.

14. The product according to claim 10 wherein
the PEG-10 olive glyceride is present in an amount of 4 weight percent;
the lauryl alcohol is present in an amount of 1.5 weight percent; and
the quaternium-87, propylene glycol is present in an amount of 11 weight percent.

15. The product according to claim 10 wherein
the caprylic acid/capric acid triglyceride is present in an amount of 70 weight percent;
the PEG-10 olive glyceride is present in an amount of 2 weight percent;
the myristyl alcohol is present in an amount of 3 weight percent;
the quaternium-26, propylene glycol is present in an amount of 4 weight percent; and
the bis-ethyl(isostearylimidazoline) isostearamide is present in an amount of 4 weight percent.

16. The product according to claim 10 wherein
the caprylic acid/capric acid triglyceride is present in an amount of 30 weight percent;
the PEG-10 olive glyceride is present in an amount of 4 weight percent;
the lauryl alcohol is present in an amount of 2.5 weight percent;
the myristyl alcohol is present in an amount of 1.5 weight percent;
the quaternium-87, propylene glycol is present in an amount of 11 weight percent; and
the bis-ethyl(isostearylimidazoline) isostearamide is present in an amount of 4 weight percent.

17. The product according to claim 10 wherein
the caprylic acid/capric acid triglyceride is present in an amount of 60 weight percent;
the PEG-10 olive glyceride is present in an amount of 4 weight percent;
the lauryl alcohol is present in an amount of 5.5 weight percent; and
the quaternium-87, propylene glycol is present in an amount of 11 weight percent.

18. The product according to claim 10 wherein
the PEG-10 olive glyceride is present in an amount of 4 weight percent;
the lauryl alcohol is present in an amount of 10.5 weight percent; and
the quaternium-87, propylene glycol is present in an amount of 11 weight percent.

19. The product according to claim 10 wherein
the caprylic acid/capric acid triglyceride is present in an amount of 55 weight percent;
the PEG-10 olive glyceride is present in an amount of 2 weight percent;
the myristyl alcohol is present in an amount of 3 weight percent;
the quaternium-26, propylene glycol is present in an amount of 4 weight percent; and
the bis-ethyl(isostearylimidazoline) isostearamide is present in an amount of 4 weight percent.

20. The product according to claim 10 wherein
the caprylic acid/capric acid triglyceride is present in an amount of 46 weight percent;
the PEG-10 olive glyceride is present in an amount of 4 weight percent;
the lauryl alcohol is present in an amount of 2.5 weight percent;
the myristyl alcohol is present in an amount of 8.5 weight percent; and
the quaternium-87, propylene glycol is present in an amount of 11 weight percent.

* * * * *